United States Patent
Kronholz et al.

[11] Patent Number: 5,967,966
[45] Date of Patent: Oct. 19, 1999

[54] FLEXIBLE, ADAPTABLE PLASTIC CATHETER SYSTEM FOR INSERTING CATHETERS FOR RADIOTHERAPY AND METHOD OF USE THEREOF

[75] Inventors: Hans Kronholz, Duelmen-Buldern; Michael Schmilowski, Muenster; Christine Anders; Reinhold Brathun, both of Haltern; Lothar Heinrich; Normann Willich, both of Muenster, all of Germany

[73] Assignee: Huels Aktiengesellschaft, Marl, Germany

[21] Appl. No.: 09/102,619

[22] Filed: Jun. 23, 1998

Related U.S. Application Data

[62] Division of application No. 08/685,944, Jul. 22, 1996, Pat. No. 5,803,895.

[30] Foreign Application Priority Data

Jul. 21, 1995 [DE] Germany .......................... 195 26 680

[51] Int. Cl.⁶ ................................................ A61M 36/04
[52] U.S. Cl. .................................................... 600/3
[58] Field of Search ............................................ 600/3–8

[56] References Cited

U.S. PATENT DOCUMENTS

| | | | |
|---|---|---|---|
| 4,754,745 | 7/1988 | Horowitz | 600/8 |
| 5,199,939 | 4/1993 | Dake et al. | 600/3 |
| 5,460,592 | 10/1995 | Langton et al. | 600/7 |

FOREIGN PATENT DOCUMENTS

| | | | |
|---|---|---|---|
| 0283071 | 10/1993 | Germany | 600/6 |

OTHER PUBLICATIONS

Haybittle et al, "British Journal of Radiology" vol. 48, No. 568 pp. 295–298, Feb. 1975.

*Primary Examiner*—William E. Kamm
*Attorney, Agent, or Firm*—Oblon, Spivak, McClelland, Maier & Neustadt, P.C.

[57] ABSTRACT

A plastic catheter system for irradiation therapy by the afterloading method, made from:
  a flexible plastic matrix having one or more catheters or sheaths embedded therein, and having a synthetic fabric contained within the plastic matrix or on a side of the plastic matrix, wherein:
    a) when the plastic matrix has all flat surfaces, the synthetic fabric is located on a side opposite the location of the one or more catheters and covers the entire side in area,
    b) when the plastic matrix is cylindrical in shape, the synthetic fabric is located in a lower portion of the cylindrical plastic matrix and coaxially arranged, and
    c) when the plastic matrix is of a shape other than a) and b), the synthetic fabric is located on a side facing away from a side from which irradiation occurs.

39 Claims, 3 Drawing Sheets

TYPE A

TYPE A

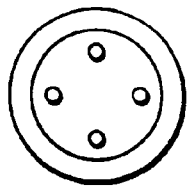
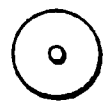
TYPE C  
*FIG. 2A*
TYPE D  
*FIG. 2B*
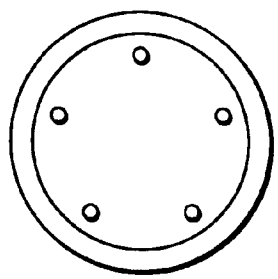
TYPE E  
*FIG. 2C*
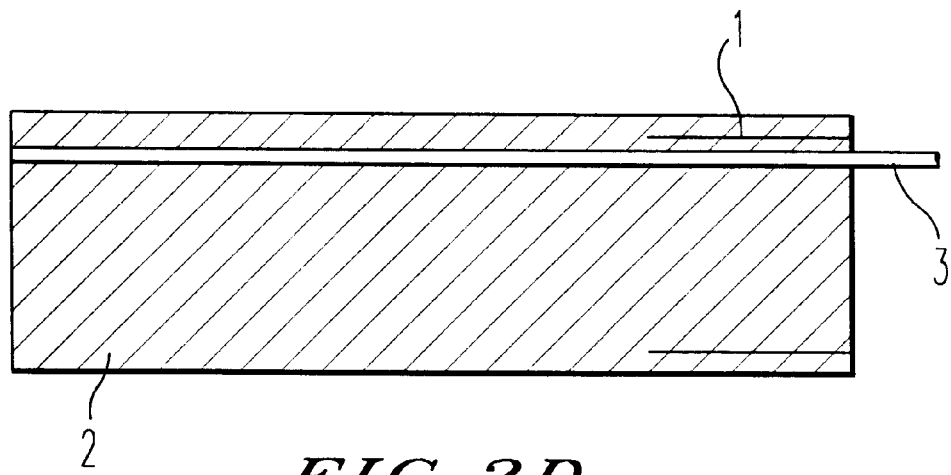
*FIG. 2D*

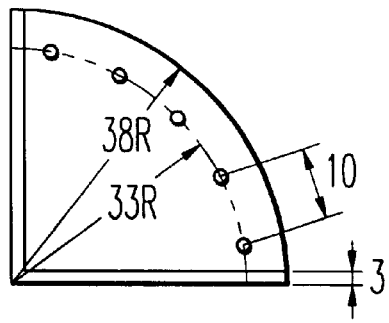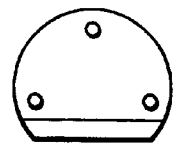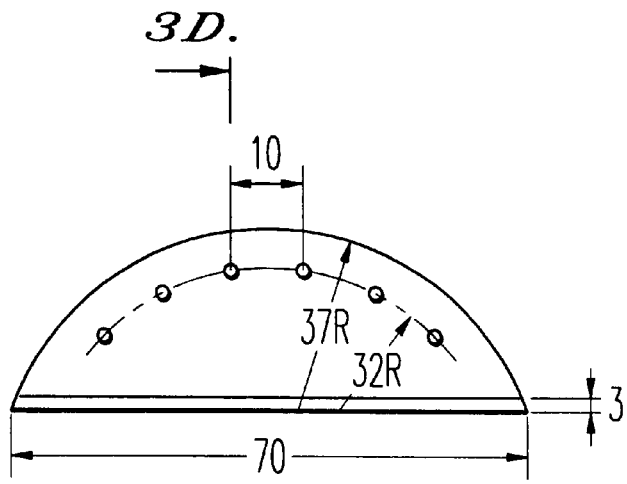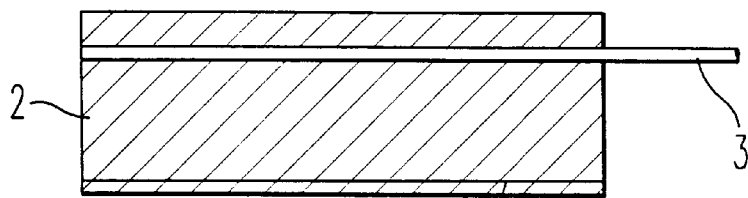

FLEXIBLE, ADAPTABLE PLASTIC CATHETER SYSTEM FOR INSERTING CATHETERS FOR RADIOTHERAPY AND METHOD OF USE THEREOF

This application is a division of application Ser. No.685, 944, filed Jul. 22 1996 and now U.S. Pat. No. 5, 803,895.

BACKGROUND OF THE INVENTION

1. Field of the Invention

The present invention relates to a plastic catheter system useful for the accurate insertion of catheters for radiotherapy by the afterloading method.

2. Discussion of the Background

Radiotherapy is of proven use for the treatment of tumors. The recognized method for radiation treatment in body cavities, such as in the throat, bowel or vaginal region, and in regions of the body opened surgically, is brachytherapy, in which one or more radiation sources is brought, controlled by an afterloading device, in a precise and metered manner to the site of treatment in the body. The radiation source is then moved to provide a previously calculated isodose contour, as described in D. E. Wazer, R. Schmidt-Ullrich, W. Chasin, A. Wu, M. Buscher, Am. J. Otolaryngology 10 (3), (1989), 173 and R. Stepan, P. Lukas, U. Fink, P. Kneschaurek, Ir. Siewert, M. Molis, "Intraoperative Radiotherapy with High Dose Afterloading (Flabs Method) in Colorectal Carcinoma", in F. W. Schildberg, N. Willich, H. -J. Krämling (Editors) "Intraoperative Radiation Therapy", Proceedings 4th International Symposium IORT, Munich 1992, Verlag Die Blaue Eule, Essen.

In order to avoid harming the patient and to guarantee the requirements for accurate irradiation, the catheters must be accurately positioned and, in addition, fixed on or in the body. Only when this is ensured can programming of the required isodose contour take place and pre-planned irradiation be guaranteed.

It must also be ensured that the mobility of the radiation sources guided by the catheters is not impaired either by kinks, constrictions or excessively severe radii of curvature of the catheters. If the radiation source becomes trapped, there may be considerable overdosage, with serious risk of harm to the patient. The emergency measures which are then necessary are those associated with unavoidable exposure of staff to radiation (Isabel Gosh, Sicherheitstechnisch bedeutsame Ereignisse an Afterloadinganlagen: Untersuchungen zur Strahlenexposition, Folgerungen zur Sicherheit von Personal und Patient [Events with relevance to safety in afterloading systems: investigations on radiation exposure, consequences for safety of staff and patient] Diplomarbeit Berufsakademie, Karlsruhe, 1991).

In the event of repeated radiation treatments, where a reduced radiation dose is given in each subsequent treatment, secure fixation of the catheters at the site of treatment over a lengthy period is particularly important. Moreover, accurate catheter fixation is necessary so that external and convenient preparation of patients who live some distance away from the radiotherapy centers is possible. In addition, this makes it possible for a much larger number of patients to be referred for radiotherapy treatment than previously possible.

The conventional practice for producing fixed catheter sets is to cut rubber-like standard flat blocks (1 to 3 cm high, area: 30×30 cm$^2$, available from Quandt Medizintechnik, Hamburg, or Mick RadioNuclear Instruments Inc., Bronx, N.Y., for example) to size and then to bore through by hand using a hollow needle in order to fit the catheters therein. These operations are time-consuming, tie up staff and result in inaccurate embedding of the catheters. For example, as the length of the needle increases, the friction on the outer wall of the needle increases, the material of the flat block deforms, and the pierced channels are no longer parallel.

In addition, these blocks containing the catheters, so-called "flabs" in the industry, cannot be securely fixed to the intended site of administration. Tears occur in the holes pierced by the fixing threads and thus the flab becomes displaced or entirely detached. This results in the catheters changing position overall or with respect to one another and the irradiation fails. It is then necessary to carry out a new localization to establish the exact displacement of the catheters. Reoperation is then often necessary, with all the additional risks associated therewith. By contrast, if the catheter fixation can be made secure, some of the patients could also be looked after at their local hospital between irradiation treatments, with a concurrent reduction in costs.

Cylindrical plastic catheter systems are likewise unavailable. Recourse is made to plastic parts with self-drilled holes, as described in the publication by D. E. Wazer et al., cited above, page 177. In the throat, recourse is made to fixation of individual catheters which are equipped with anchors and are sutured in a manner that is time-consuming and considerably stressful for the patient, as described in P. C. Levendag, L. L. Visch, N. Doiver, The Journal of Prosthetic Dentistry, 63 (6), (1990), p. 665.

U.S. Pat. No. 4,963,128 discloses a soft flab equipped with catheters, but it does not yet fully meet practical requirements. The radii of curvature of the outer catheters are small and endanger the mobility of the sources. The loops for fixing the so-called flab are readily torn and often cannot be used fully for fixation because they may be located also in regions where suturing is impossible. The extremely soft material of the flab also does not permit fundamentally secure fixation via the four loops. Furthermore, because of the geometric differences of the areas to be treated, it is necessary to store, at great cost, many different-sized flabs equipped with catheters in this way.

The flabs of the prior art can be used only for treatment points which are extensively flat or have only moderate curvature. Flabs of this design are in principle unsuitable for narrower body cavities or highly curved body and tissue surfaces.

SUMMARY OF THE INVENTION

Accordingly, one object of the present invention is to provide a plastic catheter system for radiotherapy by the afterloading method, which can be flat, suitable for the usual body cavities or suitable for highly curved treatment areas and which does not have the above-mentioned disadvantages.

A further object of the present invention is to provide a plastic catheter system that can be adapted with negligible effort to the administration conditions by simply cutting to size. Still another object of the present invention is to provide a method of treating a subject by radiotherapy using the catheter system of the present invention.

These and other objects of the present invention have been satisfied by the discovery of a plastic catheter system for irradiation therapy, comprising:

a flexible plastic matrix having one or more catheters or sheaths embedded therein, and having a synthetic fabric contained within said plastic matrix or on a side of said plastic matrix, wherein:

a) when said plastic matrix has all flat surfaces, said synthetic fabric is located on a side opposite the location of said one or more catheters and covers said entire side in area,
b) when said plastic matrix is cylindrical in shape, said synthetic fabric is located in a lower portion of said cylindrical plastic matrix and coaxially arranged, and
c) when said plastic matrix is of a shape other than a) and b), said synthetic fabric is located on a side facing away from a side from which irradiation occurs.

BRIEF DESCRIPTION OF THE FIGURES

Various other objects, features and attendant advantages of the present invention will be more fully appreciated as the same becomes better understood from the following detailed description when considered in connection with the accompanying figures in which like reference characters designate like or corresponding parts throughout the several views and wherein:

FIG. 2 is a schematic drawing of cylindrical catheter systems of Types C–E.

FIG. 3 is a schematic drawing of special shaped catheter systems of Types F–I.

DETAILED DESCRIPTION OF THE PREFERRED EMBODIMENTS

The plastic catheter system according to the present invention is equipped with a synthetic fabric above the catheters, over the entire surface and on the side facing away from the site of irradiation in the case of a flat design, and in the lower part in the case of cylindrical shapes. The present catheter system is further equipped with a synthetic fabric always on the side facing away from the irradiation in the case of other shapes. The plastic catheter system can be cut in any way to meet needs and requirements. In order for the plastic surrounding the catheters to be soft and flexible and for a liquid-tight contact between catheters and plastic matrix to be ensured the plastic material preferably has a density of from 0.9 to 1.5 g/cm$^3$ most preferablly from 0.9 to 1.2 g/cm$^3$, and is not harmful to health, as measured by the duration of administration and the severity of the indication. The plastic must also be suitable for sterilization using conventional sterilization methods.

Figure 1A:
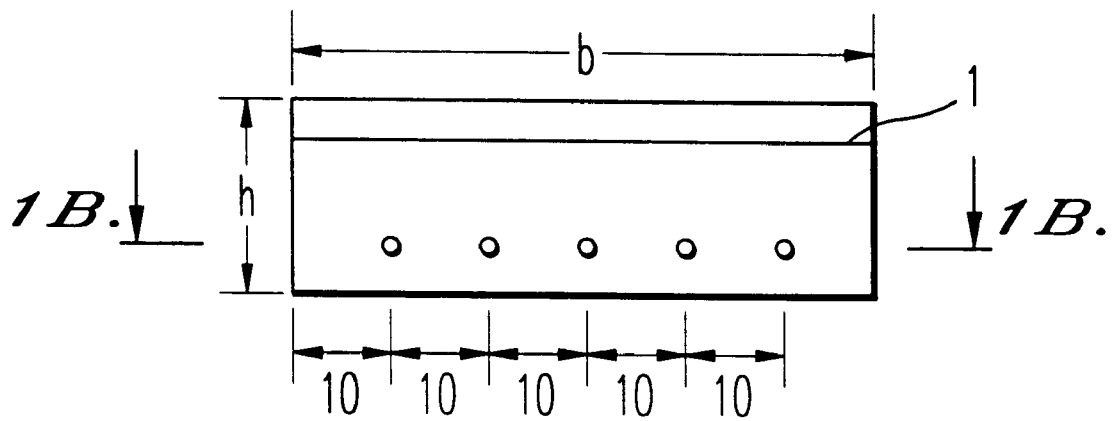
FIG. 1 is a schematic drawing of flat catheter systems of Type A showing polymeric fabric (1), polymeric body material (2) and catheter (3).
Figure 1B:
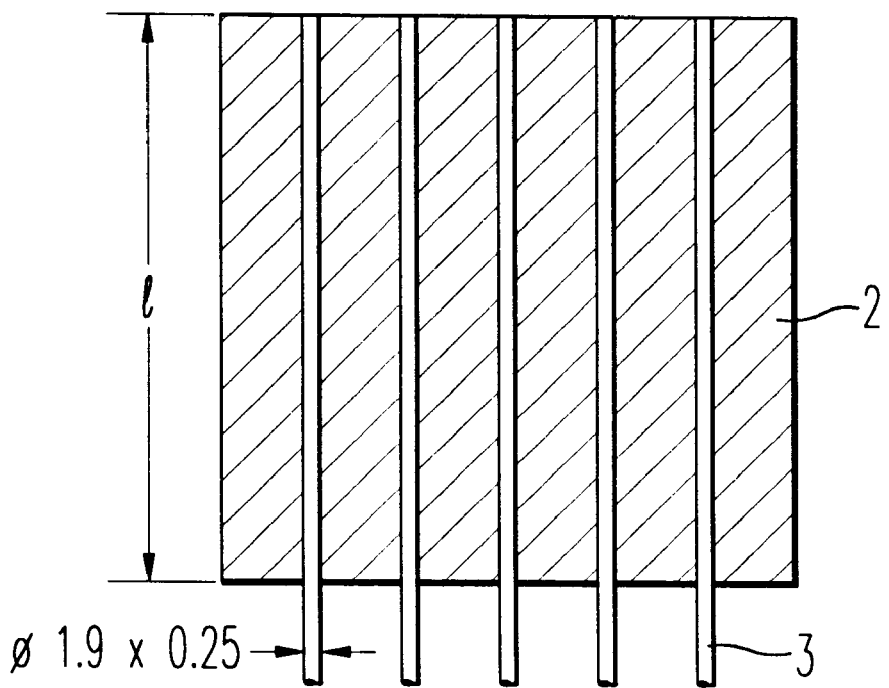

The plastic catheter system of the present invention is equipped with a non-fluffing, body-friendly synthetic fabric which is incorporated under the surface of the entire area of a flat design or with a coaxial synthetic fiber fabric on the lower part of the cylindrical bodies, in all cases on the side facing away from the irradiation area or away from the irradiation zone (see FIGS. 1–3, wherein (1) represents the synthetic fabric, (2) represents the plastic matrix, (3) represents the catheter, h represents the total height of the flab, b represents the total width of the flab and I represents the total length of the flab (within the context of the present invention, the term "non-fluffing" refers to a fabric which does not have a fuzzy surface, i.e. does not have a surface made of many fiber ends).

In a further embodiment, the synthetic material used to provide the body of the present catheter system can have incorporated therein on the side facing away from the irradiation area, one or more substances having a high atomic number (such as lead) and that provide a radiation shielding effect. The one or more additive substances can be added in an amount sufficient to maintain the flexibility of the synthetic material and to provide a shielding effect with respect to the radiation source used. The shielding effect of the one or more additive substances brings about a reduction in the radiation exposure in this region by up to 80%. By so doing, the radiation exposure of the patient can be essentially restricted to the actual focus and, in the event of the patient possibly being rescued, the radiation exposure of the staff can be decisively reduced.

Suitable synthetic materials which can be used for embedding the afterloading catheters are conventional body-friendly, soft plastics based on polyurethanes, polyolefins, polycarbonates, polyvinyl chloride, polysulfones, polyethers, polyesters, polyamides and analogous polymers and silicones with and without plasticizers, having a density in the range from 0.8 to 1.5 g/cm$^3$, preferably from 0.9 to 1.2 g/cm$^3$, a reproducible γ-ray adsorption which is as low as possible, and can be sterilized by conventional methods without the formation of harmful decomposition products. Gel-like polymer systems are also suitable. The catheters preferably consist of polyamide, but other materials are likewise acceptable.

The fabric incorporated into the plastic must consist of non-fluffing, tissue-compatible polymer fibers that can be easily cut and that provide a firm bond, free of cavities and tears, with the surrounding plastic matrix. Suitable fabrics include fabrics composed of the above-mentioned polymers and others. Glass fiber fabrics are, by contrast, unsuitable because of their tendency to form fine fragments which lead to undesirable secondary reactions and can be removed from the tissue only with difficulty. The synthetic fabrics used in the present invention can be sewn directly onto the body tissue.

The plastic catheter system according to the present invention can be used directly in the basic shapes or else cut to size as required, in which case care must be taken that the catheters are cut straight. When flexible sheaths are used it is necessary, as position holder for the catheters in the flab, to insert the catheters and glue them flush in the guide tube. The open catheter ends should be closed with a plug of the same material. This takes place either by heating the plug to the softening point in accordance with the instructions of the manufacturer of the catheter, or they should be closed with heated flat pliers so that a right-angled closure takes place without additional constriction. Closure with a tissue-compatible binder, such as with Scotch-Weld DP 490 (3 M) or Vitralit 6127 (Panacol Elosol) is also possible.

Another essential advantage of the plastic catheter system of the present invention is that it can be fixed at any point with any modification of the geometric shape, and the formation of continuous tears in the pierced holes is precluded by the fabric used. Thus, slipping is avoided.

The plastic catheter systems according to the invention are depicted in their fundamental shapes A to I and standard dimensions in FIGS. 1–3.

Users have the greatest interest in dimensions of 100×100 mm and 300×300 mm and thicknesses of 3, 5, 10 and 20 mm (Type A in FIG. 1) for flat plastic catheter systems. The embedded catheters can, in the closed state, terminate directly at the edge of the plastic or pass through the plastic matrix and have an open termination outside.

The latter may apply in particular when the plastic catheter systems according to the invention are produced in series using continuous catheters. Before use, the open side should be shortened and closed appropriate for use, as the side intended for the irradiation is located below the catheter arrangement.

FIG. 2 shows cylindrical plastic catheter systems of Types C–E having different dimensions, that are appropriate for radiotherapy applications and are produced as standard types as required. Type I (FIG. 3) also basically belongs thereto, in this case only depicted in top view. All these cylindrical types C–E and Type I are equipped with a coaxial cylindrical fabric insert (1) on one side at the catheter entry side. With these plastic catheter types too, the catheter has a closed termination at one end on the plastic matrix face or passes through it and has an open termination.

Types F–H in FIG. 3 are examples of special shapes suitable as basic bodies for body cavities with specific shapes.

Any other shapes are also possible starting from the basic types A to I, for example, after provision of a model body and also with a course of the catheters which is not a straight line but accurately fixed. According to the present invention it is also possible for such shapes to be adapted accurately by cutting and equipped with a polymer fabric insert.

Having generally described this invention, a further understanding can be obtained by reference to certain specific examples which are provided herein for purposes of illustration only and are not intended to be limiting unless otherwise specified.

EXAMPLES

Application Examples

1. A young man, 25 years old, with an ectosteal, small-cell, malignant tumor, most probably PNET, on the median left thigh. Previously, he had received 6 courses of chemotherapy, and preoperative radiation of the left thigh up to 54 Gy.
   Now: After reduction in the size of the tumor by the previous therapy, en bloc resection of the tumor with attached osseous lamella and intraoperative high-dose rate afterloading radiation with iridium-192 in the region of the tumor bed was administered.
   A single dose of 10 Gy at a tissue depth of 0.5 cm was metered, provided from the cranial direction and at a total length of 18 cm. The patient tolerated the radiation well, without complications. No infections and no impairments of wound healing occurred.

2. Young man, 34 years old, with a mucoepidermoid carcinoma in the region of the base of the tongue, initially inoperable. He had received previous percutaneous radiation up to 70 Gy and previous interstitial brachytherapy with a total focal dose of 10 Gy.
   Now: the tumor was progressing after completion of radiation. For local dose saturation, the base of the tongue and the hypopharyngeal region underwent radiation twice by flab application. This entailed application of 2×5 Gy over a distance of 5 cm based on a depth of 0.5 cm of tissue. The patient tolerated the new radiation well with negligible side effects.

Explanation of the Figures:

The dimensions of the plastic catheter systems presented here are only by way of example, and the systems are by no means restricted to these.

| Type | b (mm) | l (mm) | h (mm) (shown as height above/height below the non-woven material, including the catheter) | Number of catheters |
|---|---|---|---|---|
| A (Ex. 7) | 100 | 100 | 3/5 | 5 |
| A (Ex. 2) | 200 | 200 | 10/20 | 19 |

| Part No. | Name |
|---|---|
| 1 | Fabric, e.g., 100 × 0.4 × 100 |
| 2 | Soft polymer, e.g., 100 × 20 × 100 |
| 3 | Catheter, e.g., 1.9 × 0.25 × 400 and longer |

| Type | Part No. | Name |
|---|---|---|
| C | 1 | Fabric, e.g., 50 × 0.4 × 25 |
|   | 2 | Soft polymer, e.g., Ø 20 × 100 |
|   | 3 | Catheter, e.g., 1.9 × 0.25 × 100 and longer |
| D | 1 | Fabric, e.g., 30 × 0.4 × 25 |
|   | 2 | Soft polymer, e.g., Ø 10 × 200 |
|   | 3 | Catheter, e.g., 1.9 × 0.25 × 400 and longer |
| E | 1 | Fabric, e.g., 81 × 0.4 × 25 |
|   | 2 | Soft polymer, e.g., Ø 30 × 200 |
|   | 3 | Catheter, e.g., 1.9 × 0.25 × 400 and longer |
| F–I | 1 | Fabric, e.g., 65 × 0.4 × 65 |
|   | 2 | Soft polymer, e.g., 70 × 20 × 90 |
|   | 3 | Catheter, e.g., 1.9 × 0.25 × 400 and longer |

This application is based on German Patent Application 195 26 680.3, filed with the German Patent Office on Jul. 21, 1995, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A plastic catheter system for irradiation therapy, comprising:
   a flexible plastic matrix having at least one catheter embedded therein, and having a synthetic fabric within said plastic matrix, wherein said plastic matrix is shaped such that it has all flat surfaces, and said synthetic fabric is located on a flat surface of the catheter system such that when the catheter system is positioned in the human body, the fabric bearing surface faces away from the flat surface of the catheter system which is exposed to radiation.

2. The plastic catheter system as claimed in claim 1, wherein the plastic matrix has a density of from 0.8 to 1.5 g/cm$^3$.

3. The plastic catheter system as claimed in claim 2, wherein the plastic matrix has a density of from 0.9 to 1.2 g/cm$^3$.

4. The plastic catheter system as claimed in claim 1, wherein the plastic matrix comprises a plastic selected from the group consisting of polyurethanes, polyolefins, polycarbonates, polyvinyl chloride, polysulfones, polyethers, polyesters, polyamides, and silicones, with and without plasticizers.

5. The plastic catheter system as claimed in claim 1, wherein said synthetic fabric is formed of non-fluffing, cuttable, tissue-compatible polymer fibers.

6. The plastic catheter system as claimed in claim 5, wherein said polymer of the fiber is selected from the group consisting of polyurethanes, polyolefins, polycarbonates, polyvinyl chloride, polysulfones, polyethers, polyesters, polyamides, and silicones.

7. The plastic catheter system as claimed in claim 1, wherein said high atomic number material is lead particles.

8. The plastic catheter system as claimed in claim 1, wherein said at least one catheter terminate directly at a flat surface of the plastic matrix.

9. The plastic catheter system as claimed in claim 1, wherein said at least one or more catheter passes through the plastic matrix and has an open termination outside of said plastic matrix.

10. The plastic catheter system as claimed in claim 1, wherein the system has a plurality of catheters, all arranged equidistant from one another.

11. The plastic catheter system as claimed in claim 1, wherein said plastic matrix material contains a high atomic number material therein on a flat surface of the plastic catheter system such that when the catheter system positioned in the human body, said flat surface faces away from the body area to be irradiated.

12. The plastic catheter system as claimed in claim 1, wherein the flexible plastic matrix containing said at least one catheter in cut into a required shape in order to place into a human body.

13. A plastic catheter system for irradiation therapy, comprising:

a flexible plastic matrix having at least one catheter embedded therein, and of a shape such that it has all flat surfaces and a synthetic fabric located on a flat surface of the catheter system such that when the catheter system is positioned in the human body, the fabric bearing surface faces away from the flat surface of the catheter system which is exposed to radiation.

14. The plastic catheter system as claimed in claim 13, wherein the plastic matrix has a density of from 0.8–1.5 g/cm$^3$.

15. The plastic catheter system as claimed in claim 14, wherein the plastic matrix has a density of from 0.9–1.2 g/cm$^2$.

16. The plastic catheter system as claimed in claim 13, wherein the plastic matrix comprises a plastic selected from the group consisting of polyurethanes, polyolefins, polycarbonates, polyvinyl chloride, polysulfones, polyethers, polyesters, polyamides and silicones, each optionally plasticized.

17. The plastic catheter system as claimed in claim 13, wherein said synthetic fabric is formed of non-fluffing, cuttable, tissue-compatible polymer fibers.

18. The plastic catheter system as claimed in claim 17, wherein said synthetic polymer of the fibers of the fabric is selected from the group consisting of polyurethanes, polyolefins, polycarbonates, polyvinyl chloride, polysulfones, polyethers, polyesters, polyamides and silicones, each optionally plasticized.

19. The plastic catheter system as claimed in claim 13, wherein said plastic matrix material contains a high atomic number material therein on a flat surface of the plastic catheter system such that when the catheter system is positioned in the human body, said flat surface faces away from the body area to be irradiated.

20. The plastic catheter system as claimed in claim 13, wherein said high atomic number material is lead particles.

21. The plastic catheter system as claimed in claim 13, wherein said at least one catheter terminates directly at a flat surface of the plastic matrix.

22. The plastic catheter system as claimed in claim 13, wherein said at least one catheter passes through the plastic matrix and has an open termination outside of said plastic matrix.

23. The plastic catheter system as claimed in claim 13, wherein the system has a plurality of catheters, all arranged equidistant from one another.

24. The plastic catheter system as claimed in claim 13, wherein the flexible plastic matrix containing said at least one catheter is cut into a required shape in order to place into a human body.

25. A plastic catheter system for irradiation therapy, comprising:

a flexible plastic matrix of a cylindrical shape having at least one catheter embedded therein and having a coaxially positioned synthetic fabric inserted in the plastic matrix from the end of the cylinder at which the at least one catheter of the system enters the cylinder.

26. The plastic catheter system as claimed in claim 25, wherein the plastic matrix has a density of from 0.8–1.5 g/cm$^3$.

27. The plastic catheter system as claimed in claim 26, wherein the plastic matrix has a density of from 0.9–1.2 g/cm$^2$.

28. The plastic catheter system as claimed in claim 25, wherein the plastic matrix comprises a plastic selected from the group consisting of polyurethanes, polyolefins, polycarbonates, polyvinyl chloride, polysulfones, polyethers, polyesters, polyamides and silicones, each optionally plasticized.

29. The plastic catheter system as claimed in claim 25, wherein said synthetic fabric is formed of non-fluffing, cuttable, tissue-compatible polymer fibers.

30. The plastic catheter system as claim ed in claim 29, wherein said synthetic polymer of the fibers of the fabric is selected from the group consisting of polyurethanes, polyolefins, polycarbonates, polyvinyl chloride, polysulfones, polyethers, polyesters, polyamides and silicones, each optionally plasticized.

31. The plastic catheter system as claimed in claim 25, wherein said plastic matrix material contains a high atomic number material therein on a flat surface of the plastic catheter system such that when the catheter system is positioned in the human body, said flat surface faces away from the body area to be irradiated.

32. The plastic catheter system as claimed in claim 25, wherein said high atomic number material is lead particles.

33. The plastic catheter system as claimed in claim 25, wherein said at least one catheter terminates directly at a flat surface of the plastic matrix.

34. The plastic catheter system as claimed in claim 25, wherein said at least one catheter passes through the plastic matrix and has an open termination outside of said plastic matrix.

35. The plastic catheter system as claimed in claim 25, wherein the system has a plurality of catheters, all arranged equidistant from one another.

36. The plastic catheter system as claimed in claim 25, wherein the flexible plastic matrix containing said at least one catheter is cut into a required shape in order to place into a human body.

37. A method, comprising:
   receiving the plastic catheter system of claim 1 in the desired position in the human body by sewing the fabric of the catheter system to selected human body tissue.

38. A method, comprising:
   receiving the plastic catheter system of claim 13 in the desired position in the human body by sewing the fabric of the catheter system to selected human body tissue.

39. A method, comprising:
   receiving the plastic catheter system of claim 25 in the desired position in the human body by sewing the fabric of the catheter system to selected human body tissue.

* * * * *